US004001602B2

United States Statutory Invention Registration [19]

[11] Reg. Number: H1602

[45] Published: Oct. 1, 1996

Brock

[54] SELF-ADHERING DISPOSABLE ABSORBENT ARTICLE

[76] Inventor: Cheryl K. Brock, The Procter & Gamble Company, Winton Hill Technical Center, 6100 Center Hill Ave., Cincinnati, Ohio 45224

[21] Appl. No.: 414,266

[22] Filed: Mar. 31, 1995

[51] Int. Cl.[6] ..... A61F 13/15

[52] U.S. Cl. ..... 604/387; 604/389; 604/355

[58] Field of Search ..... 604/355–357, 604/363–366, 386–389

[56] References Cited

U.S. PATENT DOCUMENTS

| | | | |
|---|---|---|---|
| 3,438,371 | 4/1969 | Fischer et al. | 128/156 |
| 3,570,491 | 3/1971 | Sneider | 604/366 |
| 3,906,952 | 9/1975 | Zamist | 128/290 R |
| 4,072,151 | 2/1978 | Levine | 128/290 R |
| 4,233,978 | 11/1980 | Hickey | 604/355 |
| 4,484,919 | 11/1984 | Sohn et al. | 604/358 |
| 4,596,244 | 6/1986 | Jackson | 604/389 |
| 4,753,648 | 6/1988 | Jackson | 604/389 |
| 4,758,241 | 7/1988 | Papajohn | 604/387 |
| 4,906,240 | 3/1990 | Reed et al. | 604/307 |
| 5,347,657 | 9/1994 | Unsell | 2/67 |
| 5,401,267 | 3/1995 | Couture-Dorschner et al. | 604/387 |
| 5,445,627 | 8/1995 | Mizutani et al. | 604/387 |

FOREIGN PATENT DOCUMENTS

| | | | |
|---|---|---|---|
| 4279159 | 10/1992 | Japan | 604/387 |
| WO95/16424 | 6/1995 | WIPO . | |

*Primary Examiner*—Michael J. Carone

[57] ABSTRACT

The present invention pertains to an absorbent article. The absorbent article includes a liquid pervious topsheet, a liquid impervious backsheet joined with the topsheet, an absorbent core positioned between the topsheet and the backsheet, and a periphery extending outwardly from and along the side and end edges of the absorbent core. The periphery has a body-contacting surface and a surface opposed to the body-contacting surface. The body-contacting surface of the periphery includes a continuous layer of adhesive for securing the absorbent article directly to a wearer's skin.

1 Claim, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SELF-ADHERING DISPOSABLE ABSORBENT ARTICLE

FIELD OF THE INVENTION

The present invention relates to absorbent articles such as diapers, incontinence devices, pantiliners, sanitary napkins, and the like, and more particularly to absorbent articles which adhere directly to the wearer's skin.

BACKGROUND OF THE INVENTION

The major function of absorbent articles such as disposable diapers is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist to adjacent clothing because they are not immediately absorbed within the article and the absorbent article is not able to sustain a good fit on the wearer such that gaps are created allowing the exudates to leak out of the absorbent article. For example, urine tends to be deposited onto the topsheet more rapidly than it can be absorbed and, therefore, the urine migrates to the gaps in the absorbent article where it can come in contact with clothing or other articles and can be absorbed by these articles. Additionally, loose fecal material that is not easily absorbed by the absorbent article tends to "float" on the liquid-receiving surface and work its way past the gaps in the article in the legs or waist of the wearer.

Contemporary disposable diapers have a topsheet, a backsheet, an absorbent core, and elasticized leg flaps generally formed from an elastic member being enclosed in the continuous topsheet and backsheet which extend beyond the edges of the absorbent core. These elasticized leg flaps prove effective generally to prevent wicking and overflow from the fluid laden diaper to clothing contacting the edges of the diaper in that the elasticized leg flaps present a fluid impervious barrier between the edge of the diaper and the contacting clothing, and in addition, provide a gasketing action about the legs of the wearer to maintain a seal about the leg and minimize gapping. However, leakage along the perimeter of the diaper may still occur. As the diaper is worn for longer periods of time, forces tend to act on the diaper to degrade the initial fit on the wearer. Large gaps and sagging of the diaper in the legs and waist are formed by the degradation in fit. Thus, as liquids are deposited onto the topshet, some of the liquid is not immediately absorbed through the topsheet and migrates toward the edges of the diaper where it can leak through or past the gaps in the diaper and come in contact with clothing or undergarments where it can be absorbed by and wicked into such garments.

Disposable diapers may be provided with barrier cuffs which inhibit loose fecal material or gushes of urine or liquids from soiling the wearer's clothing. The barrier cuffs restrain the free flow of this material and provide a structure to hold such material within the diaper so that as such material freely floats or flows on the topsheet of the diaper, it is contained within the ciaper. Despite the effectiveness of such structures in containing such material, it has been found that liquids can leak beyond the barrier cuffs and soil the wearer's clothing because the diaper construction does not promote a sustained fit of the diaper on the wearer. Additionally, the barrier cuffs may not be properly applied to the wearer such that good initial fit is not achieved and the sustained fit is often worse.

Therefore, it is an object of the present invention to provide a diaper with adhesive sealing means for securing the diaper directly to a user's skin to eliminate separation of the absorbent article from the user's body during wear.

It is also an object of the present invention to provide a diaper having a continuous layer of adhesive which extends about the diaper's periphery sealing the periphery from leaking.

It is further an object of the present invention to provide an adhesive that is skin-friendly and non-irritating.

These and other objects of the present invention will be more readily apparent when considered in reference to the following description and when taken in conjunction with the accompanying drawings.

SUMMARY OF THE INVENTION

The present invention provides an absorbent article comprised of a liquid pervious topsheet, a liquid impervious backsheet joined to the topsheet, and an absorbent core having side edges and end edges positioned between the topsheet and backsheet. A periphery extends outwardly from and along the side and end edges of the absorbent core. The periphery has a body-contacting surface and a surface opposed to the body-contacting surface. The body-contacting surface of the periphery includes a substantially continuous layer of adhesive for securing the absorbent article directly to a wearer's skin.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

As used herein, the term "diaper" refers to a garment generally worn by infants and incontinent persons about the lower torso of the wearer. It should be understood, however, that the present invention is also applicable to other absorbent articles such as sanitary napkins, incontinence devices and the like.

Figure 1:
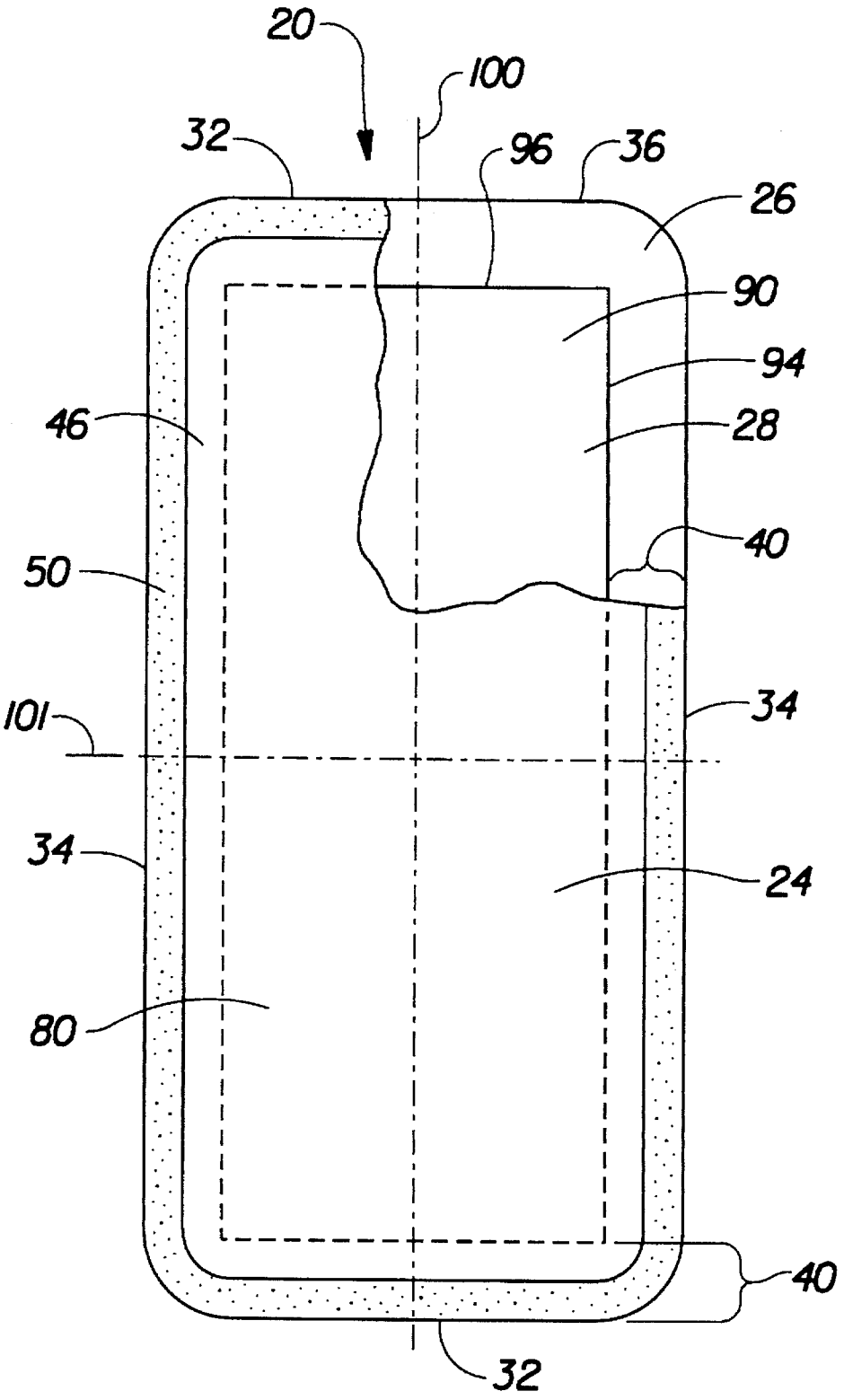
FIG. 1 is a plan view of a diaper of the present invention having portions cut away to reveal underlying structure, the body-facing surface of the diaper facing the viewer.

FIG. 1 is a plan view of the diaper 20 of the present invention in its flat-out state with portions of the structure being cut-away to more clearly show the construction of the diaper 20 and with the portion of the diaper 20 which faces or contacts the wearer, oriented towards the viewer. As shown in FIG. 1, the diaper 20 preferably comprises a liquid pervious topsheet 24, a liquid impervious backsheet 26 joined with the topsheet 24, and an absorbent core 28 positioned between the topsheet 24 and the backsheet 26.

The diaper 20 has two surfaces, a body-contacting surface or "body surface" 80 and a garment-facing surface 82 (not shown). The diaper 20 is shown in FIG. 1 as viewed from its body-contacting surface 80. The body-contacting surface 80 is intended to be worn adjacent to the body of the wearer while the garment surface 82 is on the opposite side and is intended to be positioned adjacent to the wearer's undergarments when the diaper 20 is worn. The diaper 20 has two centerlines, a longitudinal centerline 100 and a transverse centerline 101. The term "longitudinal", is as used herein, refers to a line, axis or direction in the plane of the diaper 20 that is generally aligned with (e.g., approximately parallel to) a vertical plane which bisects a standing wearer into left and fight body halves when the diaper 20 is worn. The terms "transverse" or "lateral" as used herein, are interchangeable, and refer to a line, axis or direction which lies within the plane of the diaper 20 that is generally perpendicular to the longitudinal direction.

FIG. 1 shows a preferred embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form portions of the periphery.

The absorbent core 28 may be any absorbent means which is capable of absorbing or retaining liquids (e.g., menses, urine, feces and all other bodily secretions). As shown in FIG. 1, the absorbent core 28 has a body-facing surface 90, a garment-facing surface 92 (not shown), side edges 94, and end edges 96. The absorbent core 28 may be manufactured in a wide variety of sizes and shapes (e.g., rectangular, oval, hourglass, dog bone, asymmetric, etc.) and from a wide variety of liquid-absorbent materials commonly used in diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the diaper. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264 entitled "Thin, Flexible Sanitary Napkin" issued to Osborn on Aug. 21, 1990; U.S. Pat. No. 4,610,678 entitled "High-Density Absorbent Structures" issued to Weisman et al. on Sep. 9, 1986; U.S. Pat. No. 4,834,735 entitled "High Density Absorbent Members Having Lower Density and Lower Basis Weight Acquisition Zones", issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 26 and the topsheet 24 are positioned adjacent the garment surface and the body surface, respectively, of the absorbent core 28 and are preferably joined thereto and to each other by attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 entitled "Disposable Waste-Containment Garment", which issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine and/or menses) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P 18-0401 and by Ethyl Corporation, Visqueen Division, of Terre Haute, Ind., under the designation XP-39385. The backsheet is preferably embossed and/or matte finished to provide a more cloth like appearance. Further, the backsheet 26 may permit vapors to escape from the absorbent core 28 (i.e., breathable) while still preventing exudates from passing through the backsheet 26.

The topsheet 24 is compliant, soft feeling, and non-irritating to the wearer's skin. Further, the topsheet 24 is liquid pervious permitting liquids (e.g., urine and/or menses) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet nonabsorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991. Each of these patents are incorporated herein by reference. The preferred topsheet for the present invention is the formed film described in one or more of the above patents and marketed on absorbent articles by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that fluid exudates will flow off the topsheet 24 rather than flowing into and being absorbed by the absorbent core 28. In a preferred embodiment, surfactant is incorporated into the polymeric materials of the formed film topsheet such as is described in U.S. patent application Ser. No. 08/072,660, "Absorbent Article Having A Nonwoven and Apertured Film Coversheet" filed on Jun. 4, 1993 by Aziz, et al., which is incorporated herein by reference. Alternatively, the body surface of the topsheet 24 can be made hydrophilic by treating it with a surfactant such as is described in the above referenced U.S. Pat. No. 4,950,254 issued to Osborn, incorporated herein by reference.

In a preferred embodiment of the present invention, an acquisition layer(s) may be positioned between the topsheet 24 and the absorbent core 28. The acquisition layer may serve several functions including improving wicking of exudates over and into the absorbent core. There are several reasons why the improved wicking of exudates is important, including providing a more even distribution of the exudates throughout the absorbent core and allowing the diaper 20 to be made relatively thin. (The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of absorbent articles disclosed herein having an acquisition layer and a topsheet 24 are more fully described in U.S. Pat. No. 4,950,264 issued to Osborn and U.S. patent application Ser. No. 07/944,764, "Absorbent Article Having Fused Layers", filed Oct. 7, 1992, in the names of Cree, et al. Each of these references are incorporated herein by reference. In a preferred embodiment, the acquisition layer may be joined with the topsheet by any of the conventional means for joining webs together, most preferably by fusion bonds as is more fully described in the above-referenced Cree application.

FIG. 1 also shows that the diaper 20 has a periphery 40. The periphery 40 of the diaper 20 extends generally outwardly from and along the side edges 94 and end edges 96 of the absorbent core 28 to the longitudinal side edges 34 and the end edges 32, respectively, of the diaper 20. The periphery 40 has a body-contacting surface 46 and a garment surface 48 (not shown) which is opposed to the body-contacting surface 46 of the periphery 40. The body-contacting surface 46 includes a continuous layer of adhesive 50 for securing the diaper 20 directly to a wearer's skin. The layer of adhesive 50 may cover the entire periphery or only a portion of the periphery as shown in FIG. 1. Any adhesive or glue used in the art for securing absorbent articles to the skin can be used for the adhesive herein, with pressure-sensitive adhesives being preferred.

The body-contacting adhesive 50 is typically covered with a removable release liner in order to keep the adhesive from drying out. (Embodiments are contemplated wherein the release liner is integral with the package comprising the absorbent article and thus, is not a separate liner that must be removed before use.) Suitable release liners are also described in U.S. Pat. No. 4,917,697. Any commercially available release liners commonly used for such purposes can be utilized herein. Non-limiting examples of suitable release liners are manufactured by the Akrosil Corporation of Menasha, Wis. under the designations BL30MG-A Silox E1/0 and BL30MG-A Silox 4P/0. The diaper 20 of the present invention is used by removing the release liner and thereafter properly placing the diaper so that the adhesive contacts the skin of the wearer. The adhesive 50 maintains the diaper in its position against the body of the wearer during use.

Figure 2:
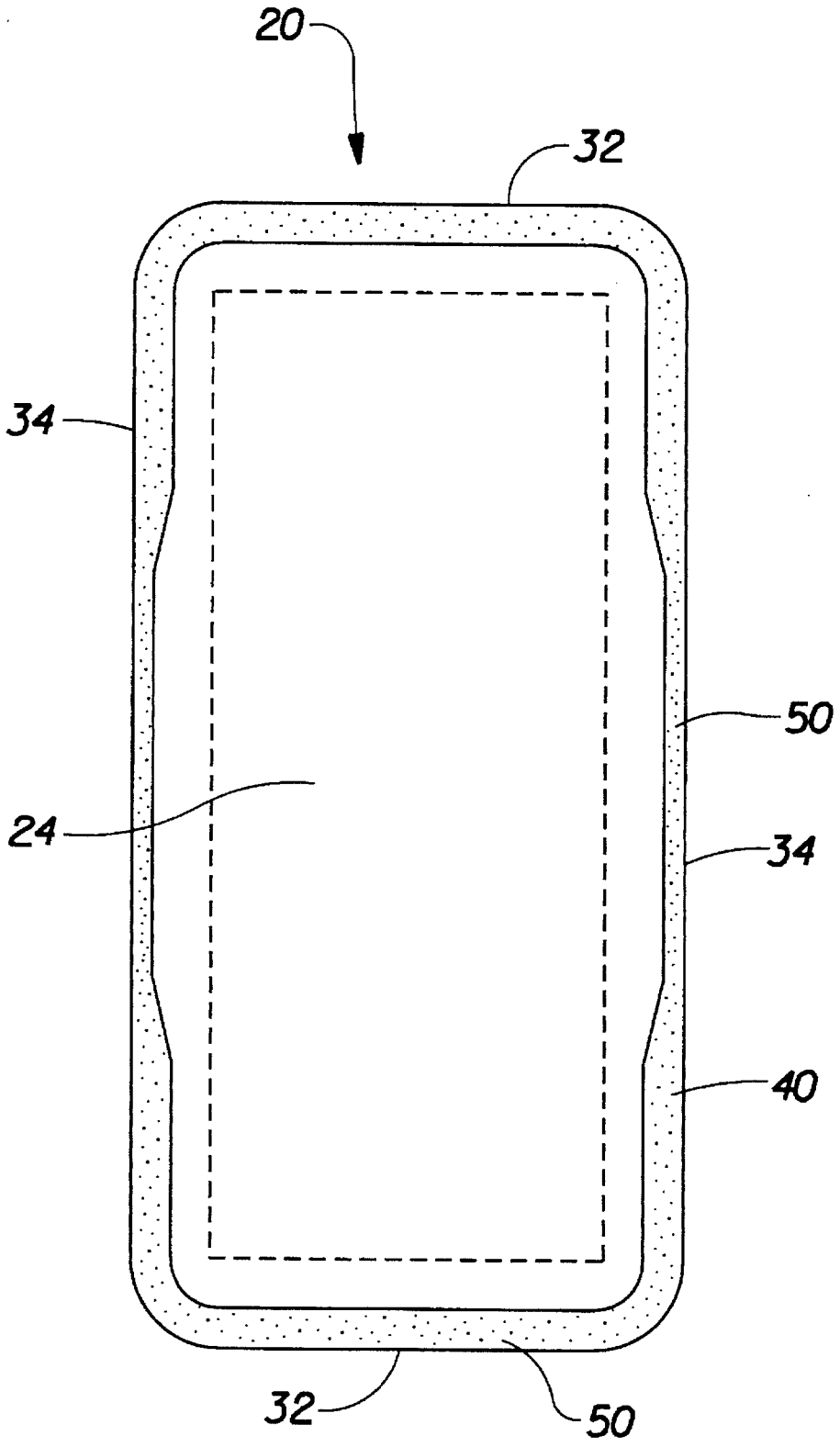
FIG. 2 is a plan view of another embodiment of a diaper of the present invention wherein an optional adhesive design is presented, the body-facing surface of the diaper facing the viewer.

FIG. 2 is a plan view of another diaper 20 embodiment of the present invention in which an optional adhesive configuration 50 is provided. As can be seen in FIG. 2, the width of the adhesive 50 is not uniform about the periphery 40 of the diaper. The adhesive has its widest dimension along the end edges 32 and the portions of the side edges 34 adjacent to the end edges 32. The adhesive has its narrowest dimension along the side edges in the central portion of the diaper.

Figure 3:
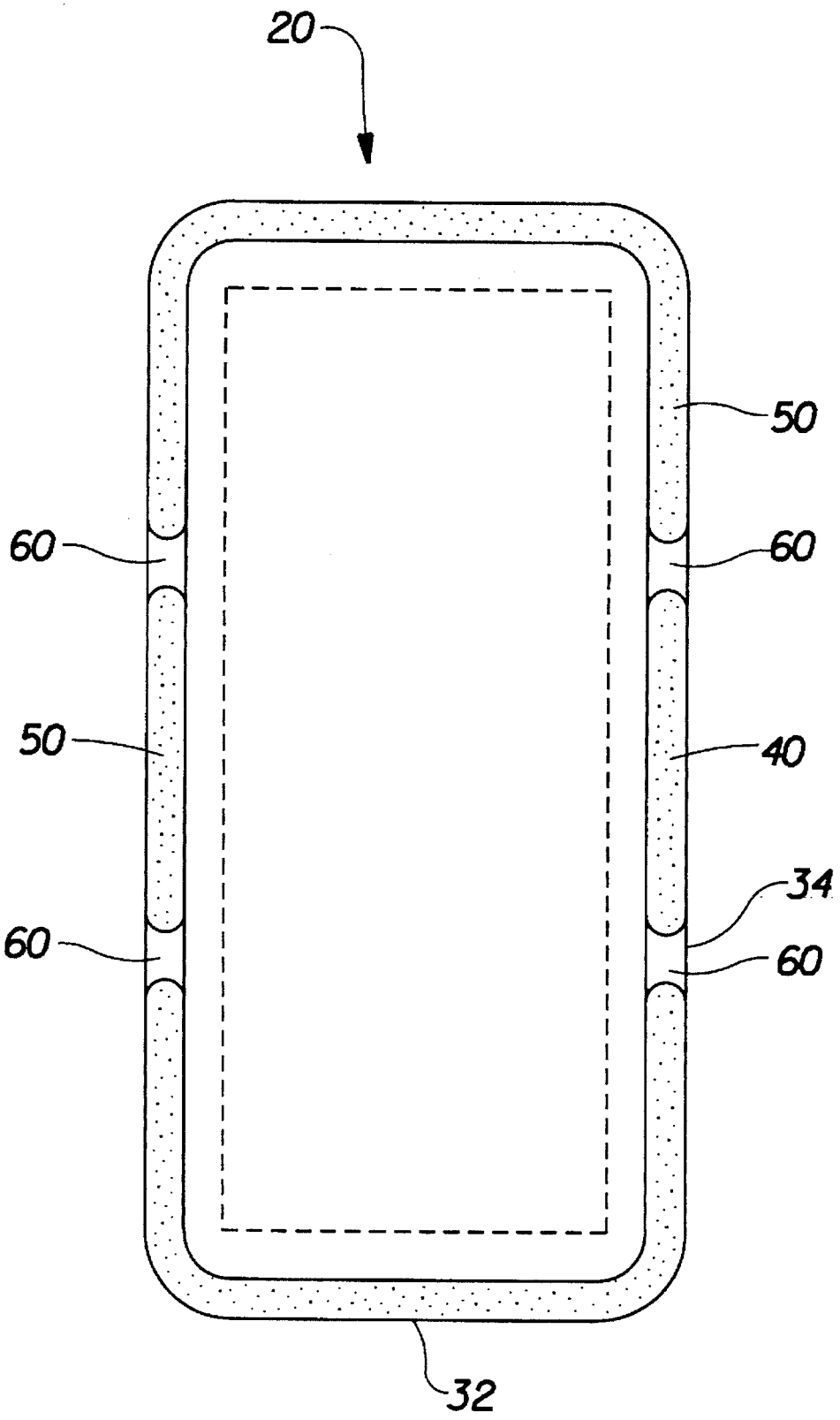
FIG. 3 is a plan view of another embodiment of a diaper of the present invention wherein an optional adhesive design is presented, the body-facing surface of thediaper facing the viewer.

FIG. 3 is a plan view of another diaper 20 embodiment of the present invention in which an optional adhesive configuration 50 is provided. The adhesive 50 is substantially continuous as it extends about the periphery 40 of the diaper 20. The adhesive 50 is discontinuous such that the periphery 40 has two nonadhesive portions 60 along each side edge 34.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

a liquid pervious topsheet;

a liquid impervious backsheet joined with said topsheet;

an absorbent core having side edges and end edges positioned between said topsheet and said backsheet; and a periphery extending outwardly from and along said side edges and said end edges of said absorbent core, said periphery having a body-contacting surface and a surface opposed to said body contacting surface, said body-contacting surface of said periphery including a continuous layer of adhesive for securing said absorbent article directly to a wearer's skin, and a removable release liner covering said continuous layer of adhesive.

* * * * *